US00PP18456P2

(12) United States Plant Patent
Carroll

(10) Patent No.: US PP18,456 P2
(45) Date of Patent: Jan. 22, 2008

(54) ***LAGERSTROEMIA* PLANT NAMED 'TRURED'**

(50) Latin Name: *Lagerstroemia (indica×fauriei)*
Varietal Denomination: Trured

(75) Inventor: Russell Howell Carroll, Glenmora, LA (US)

(73) Assignee: Plant Development Services Inc., Loxley, AL (US)

( * ) Notice: Subject to any disclaimer, the term of this patent is extended or adjusted under 35 U.S.C. 154(b) by 0 days.

(21) Appl. No.: 11/500,205

(22) Filed: Aug. 7, 2006

(51) Int. Cl.
*A01H 5/00* (2006.01)

(52) U.S. Cl. ..... Plt./252

(58) Field of Classification Search ..... Plt./252
See application file for complete search history.

*Primary Examiner*—Kent Bell
*Assistant Examiner*—S. B. McCormick-Ewoldt

(57) ABSTRACT

A new and distinct variety of *Lagerstroemia* (*indica×fauriei*) plant named 'Trured', characterized by its large, upright, dense and globose growth habit, fast growth rate, large panicles of deep red flowers and its long bloom period.

1 Drawing Sheet

Genus species: *Lagerstroemia* (*indica×fauriei*).
Varietal denomination: 'Trured'.

BACKGROUND OF THE INVENTION

The present invention relates to a new and distinct variety of Crapemyrtle of the genus *Lagerstroemia* and a member of the Lythraceae family. This new Crapemyrtle variety, hereinafter referred to as 'Trured' was discovered by Russell Howell Carroll in June, 1999. 'Trured' was found as a plant within the progeny of a controlled open pollination of *Lagerstroemia* (*indica×fauriei*) 'Tuskegee' (unpatented). Mr. Carroll found the seedling at in North Zulch, Tex. The value of this new cultivar lies in its large, upright, dense and globose growth habit, fast growth rate, large panicles of deep red flowers, and its long bloom period. The new variety has retained many of the outstanding attributes of its parent cultivar, in particular its tolerance of heat, drought, and a wide range of soil types, which makes it adaptable to culture in most of the Sunbelt States. As with the parent cultivar, the plant of this invention may be advantageously employed as a specimen appointment, a multiple or single stemmed large shrub to medium-sized tree, and is quite attractive in mass plantings.

Asexual propagation of the new plant by cuttings has been under Mr. Carroll's direction in North Zulch, Tex., where the new variety was found, as well as his current residence in Glenmora, La. The new plant retains its distinctive characteristics and reproduces true to type in successive generations. The plant cannot be reproduced true from seed.

SUMMARY OF THE INVENTION

The following are the most outstanding and distinguishing characteristics of this new cultivar when grown under normal horticultural practices in North Zulch, Tex. and Glenmora, La.

1. Deciduous, multiple, or single stemmed large shrub to medium-sized tree.
2. Large, upright, dense and globose in nature.

3. Fast growth rate under normal fertilization and moisture conditions.
4. Large panicles of deep red flowers are produced from early June into the fall.
5. Immature foliage has an attractive red color which quickly matures to dark green.
6. Mature foliage changes to an attractive yellow, orange and red color in the fall.
7. Attractive trunk structure when small lower limbs are removed.
8. The grayish colored bark exfoliates to reveal a beige coloration.
9. Attractive trunk and stem structure during the winter.
10. Adaptable to a wide range of soil types from acidic to alkaline and sand to clay.
11. Heat and drought tolerant.
12. Easily propagated with softwood cuttings in the spring and summer.
13. Tolerates full sun.
14. Hardy to Zone 7b.
15. Relatively pest resistant.
16. Performs well as a flowering street tree.
17. Good specimen plant.
18. Desirable in large planters.
19. Makes a very good large hedge or border when planted in groups.
20. Does well in mass plantings in parks, gardens, and highway beautification projects.
21. Can be used as a flowering shade tree near patios, walkways and entrances.

DESCRIPTION OF THE DRAWINGS

This new *Lagerstroemia* (*indica×fauriei*) variety is illustrated by the accompanying photographic prints in which:

1. The photograph at the top of the sheet is a close-up showing the flowers, buds, foliage and stem color, as well as flower size and form.

2. The photograph at the bottom of the sheet shows the upright, dense and globose growth habit of a seven gallon plant.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of Crapemyrtle based on my observations made of two year old plants grown in five gallon containers in commercial production practices, in greenhouses, and in established landscape plantings in North Zulch, Tex. and Glenmora, La.

Distinctive Characteristics:

TABLE 1

| Characteristic | *Lagerstroemia* X 'Trured' | *Lagerstroemia* X 'Tuskegee' | *Lagerstroemia* X 'Natchez' |
|---|---|---|---|
| Height (Mature) | 18-20' | 18-20' | 25-30' |
| Width (Mature) | 20-25' | 20-25' | 30-35' |
| Leaf Length | 1¾-2¾" | 1¾-2¾" | 1½-3" |
| Leaf Width | 1¼-1¾" | 1¼-1¾" | ¾-1½" |
| Flower Color | Red-Purple G. 60B | Red-Purple G. 68A | White G. 155D |
| Bloom Period | Early June-Sept. (Approximately 120 days) | Mid June-Sept. (Approximately 100 days) | Mid June-Sept. (Approximately 110 days) |
| Growth Habit | Upright, dense & Globose | Upright Broad & Spreading (Vase shaped) | Upright Broad |
| Bark Color (Underlying) | Grey-Brown G. 199D | Grey-Brown G. 199D | Greyed-Orange G. 165A |

Each of the cultivars, 'Trured', 'Tuskegee', and 'Natchez' are cultivars of Lythraceae *Lagerstroemia* (*indica*×*fauriei*). The author of the genus name *Lagerstroemia* and the species name *indica* is Carolus Linnaeus (1707–1778). The author of the species name *fauriei* is Bernhard Abalbert Koehne (1848–1918). *Lagerstroemia indica* is indigenous to China, whereas *Lagerstroemia fauriei* comes from Yakushima Island, Japan.

In 1962, the United States National Arboretum began an extensive Crapemyrtle breeding and selection program. Crosses between *Lagerstroemia indica* and *Lagerstroemia fauriei* were made in 1964 and between 1978 and 1990, approximately 20 cultivars were released. *Lagerstroemia* (*indica*×*fauriei*) 'Natchez' (unpatented) was officially named and released in July, 1978. *Lagerstroemia* (*indica*×*fauriei*) 'Tuskegee' (unpatented) was released in 1986. These new cultivars retained the superior flowering attributes of *Lagerstroemia indica* and the mildew resistance, exfoliating bark, and fall foliage color of *Lagerstroemia fauriei*. 'Tuskegee' is the female or seed parent of the new variety 'Trured'. 'Trured' not only retained the aforementioned attributes but also has a more upright, dense and globose growth habit, deeper red flower color, and a longer blooming period.

Classification:

*Botanical.*—*Lagerstroemia* (*indica*×*fauriei*) 'Trured'.

*Parentage.*—Openly pollinated seedling of *Lagerstroemia* (*indica*×*fauriei*) 'Tuskegee'.

*Commercial.*—Deciduous tree or shrub.

*Form.*—Upright, dense and globose.

*Height.*—18–20'.

*Width.*—20–25'.

*Growth rate.*—Fast under normal fertilization and moisture conditions. Softwood cuttings taken in the spring and summer produce rooted cuttings in 1 to 2 months in North Zulch, Tex. and Glenmora, La. Root development is vigorous and finely branched. These 12" tall cuttings planted in 5 gallon containers in the fall are 4 to 5 feet tall with profuse flowering the following year. The plant normally grows at the rate of about 3–4 feet per year and reaches a height of 20 feet and a spread of 25 feet at maturity. Although upright growth is produced the plant maintains a dense habit due to the abundant side branch development. With age the plant becomes more globose.

*Foliage.*— Alternate to subopposite, simple, deciduous, elliptic and varying in size from 1¾" to 2¾" long and 1¼" to 1¾" wide. The apex is acuminate and the base is cuneate. The margins are entire, turned upward and slightly undulate. Leaf veination is pinnate. The petioles are ⅛" to 3⁄16" long, 1⁄16" to ⅛" in diameter and puberulent. Midveins and laterals are puberulent and prominent on the upper surface and undersurface. Immature petioles, upper surface midveins and leaf margins are Greyed-Purple Group 185A. The petioles mature to Green Group 137B and the margins mature to Yellow-Green Group 147A. Immature lateral veins are Yellow-Green Group 145D upper surface and undersurface and mature to Yellow-Green Group 145C upper surface and undersurface. Immature midveins are also Yellow-Green Group 145D undersurface. Mature midveins are Yellow-Green Group 145C upper surface and undersurface. These immature foliage colors last three to four weeks in Glenmora, La. New leaves emerge glossy, glabrous and pronounced with a reddish pigmentation Greyed-Purple Group 185A upper surface and undersurface. This immature foliage matures to Yellow-Green Group 147A upper surface and Green Group 137C undersurface in one to two weeks in Glenmora, La. Mature upper surface is glossy and glabrous and the undersurface is matte. Mature foliage color persists until the onset of cool weather in the fall. At this point the leaf color changes to Yellow-Orange Group 20A, Orange-Red Group 34A and Red Group 53B with all colors interspersed. These colors persist until the leaves fall.

In 2004, the date of initial spring growth was March 14, in Glenmora, La. After the initial spring flush there was almost continuous growth until fall, ending October 15, also in Glenmora, La. This growth pattern was identical to the parent cultivar. When grown in full sun, the internode length of this plant is ¾" to 1½". When grown in light shade the internode length is 1⅛" to 1⅞". As would be expected, a plant grown in the shade results in a taller, less dense plant with larger leaves.

Stems: The young shoots are slender, angled, glabrous and have a reddish pigmentation, Greyed-Purple Group 185A, when exposed to direct sunlight. Young shoots which are shaded from direct sunlight are Yellow-Green Group 144B. This new growth becomes Greyed-Orange Group 165A and rounded in four to five weeks in Glenmora, La. After one or more years the stems become smooth, sinewy, Greyed-Brown Group 199C and eventually begin to exfoliate revealing the underlying color Greyed-Brown 199D. Branching habit is heavy. The pith is solid and uniform.

Flowers: Perfect, 1¼" to 1¾" in diameter, ¾" to 1" in depth, non-fragrant, borne on dense, upright glabrous, 8 to 10" high, 6 to 8" wide terminal panicles, on current season's growth from early June through September. Flowers normally open from the base of the panicle progressing upward. Each panicle has from 8 to 12 racemes which have from 3 to 21 flowers each, resulting in 200 or more flowers per panicle. A mature plant can have hundreds of panicles. Flower buds are rotund, 5/16" to ⅜" long, 5/16" to ⅜" wide and Greyed-Purple Group 185A when exposed to direct sunlight. Young buds which are shaded from direct sunlight are Yellow-Green Group 145B. Flower color is Red-Purple Group 60B front and back. The flowers are attached to pedicels which are ⅜" to ½" in length and Yellow-Green Group 144B. The peduncle of each raceme is from ⅛" to 4½" long and Yellow-Green Group 144B. Each flower has six petals that are ¾" long, ⅝" wide; the blade is cordate-orbicular and crisped. The flower has from 36 to 42 stamens, ½" long, Red-Purple Group 62B with anthers Yellow Group 20B. The pollen matures to Yellow Group 14A. The pistil is 13/16" long and Red-Purple Group 60A. Each flower has six sepals that are 3/16" long by ⅛" wide, lanceolate and fused into a calyx. The calyx is ⅜" to ½" in diameter, ⅜" to 7/16" in depth, has entire margins and acuminate tips. The outer surface of the calyx is Greyed-Purple Group 185A when exposed to direct sunlight and Yellow-Green Group 145B when shaded from direct sunlight. The inner surface is Yellow-Green Group 145C. In 2004, the blooming period began June 5, in Glenmora, La. and ended September 21. The self-cleaning blooms last eight to ten days on the plant in the garden.

Fruit: Broad-ellipsoidal six-valved dehiscent capsule, ⅜" to ½" in diameter. Summer fruit color Yellow-Green Group 143C ripens to Green Group 137A in the fall and persists as Green Group 137A through the winter.

The mature capsule opens in the fall to release 12–18 glabrous winged seeds which are ¼" to ⅜" long and Brown Group 200D.

Normal fruitset is not heavy which contributes to the long flowering period.

Culture: Grows well in a wide range of conditions. Tolerates full sun. Adaptable to a wide range of soil types from acidic to alkaline and sand to clay. Tolerates heat and drought when established. Responds well to mulching and medium applications of fertilizer. Very little pruning is needed. Ideal for coastal regions and warmer parts of the Piedmont. Cold-hardiness and resistance to diseases and insects are comparable to the parent variety. Propagated with softwood cuttings in the spring and summer.

Disease and insect resistance: Resistance to diseases and insects common to *Lagerstroemia* has not been observed.

I claim:

1. A new and distinct variety of *Lagerstroemia* plant named 'Trured', as illustrated and described.

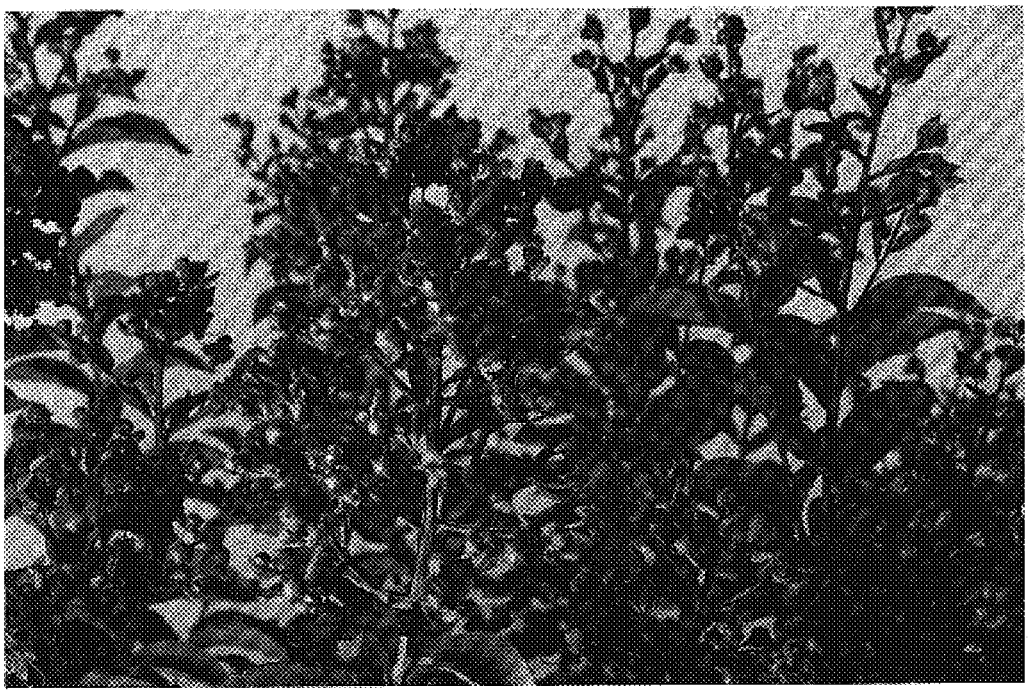
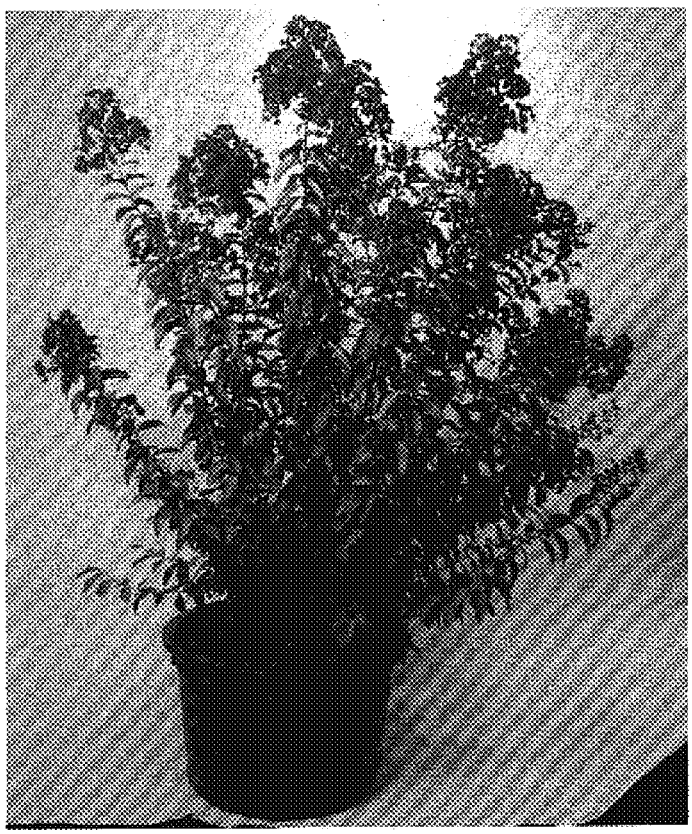

* * * * *